US00PP32810P2

(12) United States Plant Patent
Carruth

(10) Patent No.: US PP32,810 P2
(45) Date of Patent: Feb. 16, 2021

(54) FLORIBUNDA ROSE PLANT NAMED 'WEKJUCSTOKOL'

(50) Latin Name: *Rosa hybrida*
Varietal Denomination: WEKjucstokol

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 16/602,878

(22) Filed: Dec. 16, 2019

(51) Int. Cl.
*A01H 5/02* (2018.01)
*A01H 6/74* (2018.01)

(52) U.S. Cl.
USPC ..... Plt./148

(58) Field of Classification Search
USPC ..... Plt./101, 141, 148
See application file for complete search history.

(56) References Cited

U.S. PATENT DOCUMENTS

PP22,948 P3 8/2012 Austin
PP23,269 P2 12/2012 Bedard

OTHER PUBLICATIONS https://www.helpmefind.com/rose/l.php?=2.83110 (Retrieved from the Internet on Jun. 21, 2020).*

* cited by examiner

*Primary Examiner* — Susan McCormick Ewoldt
(74) *Attorney, Agent, or Firm* — McKee, Voorhees & Sease, PLC

(57) ABSTRACT

A new variety of Floribunda rose suitable for garden decoration, having flowers of medium pink coloration.

1 Drawing Sheet

Classification: The present invention relates to a new *Rosa hybrida* plant.

Variety denomination: The new plant has the varietal denomination 'WEKjucstokol'.

BACKGROUND OF THE INVENTION

This invention relates to a new and distinct variety of Floribunda Rose. It has as its seed parent the variety known as 'WEKjucistwe' (U.S. Plant Pat. No. 31,861), and as its pollen parent the variety known as 'WEKbijou' (U.S. Plant Pat. No. 23,269).

SUMMARY OF THE INVENTION

Among the features which distinguish the new variety from other presently available and commercial rose cultivars known to the inventor are the following combinations of characteristics: its strong fruity to apple-like fragrance, its old-fashioned multi-petaled flowers of medium pink coloration and its abundant blooms. The plant has an upright slightly spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKjucstokol' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKjucistwe' by the following combination of characteristics: whereas 'WEKjucstokol' bears very double flowers (about 37 to 113 petals) of medium pink coloration, 'WEKjucistwe' bears very double flowers of yellow blushing pink coloration with lesser petalage (about 45 to 65 petals). The new variety has an upright slightly spreading medium to somewhat tall growing habit (about 120 to about 160 cm. in height), whereas the seed parent has an upright moderately spreading shorter growing habit (about 95 to about 130 cm. in height).

The new variety may be distinguished from its pollen parent, 'WEKbijou' by the following combination of characteristics: whereas 'WEKjucstokol' bears very double flowers (about 37 to 113 petals) of medium pink coloration, 'WEKbijou' bears very double flowers of milk chocolate changing to lavender coloration with significantly lesser petalage (about 30 to 49 petals). The new variety has an upright slightly spreading growing habit (about 90 to about 120 cm. spread at the widest point), whereas the pollen parent has a bushy rounded significantly narrower growing habit (about 76 to about 92 cm. spread at the widest point).

COMPARISON WITH THE CLOSEST COMMERCIALLY AVAILABLE CULTIVAR

The new variety may be distinguished from its closest commercially available cultivar, 'AUSlounge' (U.S. Plant Pat. No. 22,948) by the following combination of characteristics: whereas 'WEKjucstokol' bears very double flowers (about 37 to 113 petals) with a strong fruity to apple-like fragrance, 'AUSlounge' bears double flowers with a strong spicy fragrance and with significantly lesser petalage (about 42 petals). The new variety has an upright slightly spreading growing habit (about 90 to about 120 cm. spread at the widest point), whereas the closest commercially available cultivar has a compact and bushy significantly narrower growing habit (about 90 cm. spread at the widest point).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of December. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of December. Phenotypic expression may vary with environmental, cultural and climatic conditions, as well as differences in conditions of light and soil.

FLOWER

The new variety sometimes bears its flowers singly, sometimes in clusters of two to four or more per stem. Flowers may be borne in regular rounded clusters on strong somewhat short to medium length stems (about 15 to about 55 cm.). The cluster ranges from about 12.5 to about 15.0 cm. in diameter. Outdoors, the plant blooms abundantly and nearly continuously during the growing season. The flowers have a strong fruity to apple-like fragrance.

BUD

The peduncle is about 2.6 to about 7.1 cm. in length, of somewhat slender to average caliper (about 0.2 to about 0.4 cm. in diameter), and usually erect. It is somewhat rough, with few stipitate glands, and very few hairs. Peduncle color is between 146B and 146C often heavily suffused, especially on the side exposed to the sun, with between 187B and 187C.

Before the calyx breaks, the bud is about 1.3 to about 1.6 cm. in diameter at the widest point, about 1.3 to about 1.8 cm. in length, and pointed to moderately ovoid in shape. The surface of the bud bears between 4 to 9 foliaceous with few stipitate glands and some hairs, usually with slender entire foliaceous parts extending beyond the tip of the bud about ½ or more of its length. Bud color is between 137B and 138B often heavily suffused, especially on the side exposed to the sun, with between 187B and 187A.

The sepals are 5 per flower, about 2.1 to about 4.2 cm. in length and about 0.7 to about 1.0 cm. in width at the widest point. The outer surface color of the sepal is between 137B and 138B often heavily suffused, especially on the side exposed to the sun, with between 187B and 187A. The outer surface of the sepal is moderately smooth and bears between 0 to 4 foliaceous appendages with few stipitate glands and many hairs. The inner surface color of the sepal is near 146B broadly bordered by near 139A. After the sepals open, the inner surface color is often heavily suffused, especially on the area exposed to the sun, with between 187B and 187A. The inner surface of the sepal is covered with fine wooly tomentum; sepal margins are entire and lined with few stipitate glands and numerous hairs. The sepals are moderately permanent, and usually straight in shape with acute apices.

The receptacle of the flower is of somewhat short length (about 0.5 to about 0.7 cm.) and average in caliper (about 0.7 to about 1.1 cm. in diameter). The receptacle is somewhat funnel shaped in form. Its surface is smooth with moderately thick fleshy walls. The receptacle color is between 146D and 138B.

As the petals open (after the calyx breaks), the bud is about 1.6 to about 2.3 cm. in diameter at the widest point, about 1.7 to about 2.5 cm. in length, and moderately globular to somewhat ovoid in form. The color of the under surfaces of the newly opened petals is between 59B and 60A often moderately blushed on the outermost petals with between 187A and 187B. At the point where the petal attaches, there is a moderately large zone of near 145C. The color of the upper surfaces of the newly opened petals is near 64A. At the point where the petal attaches, there is a moderately large zone of between 150C and 154C.

BLOOM

When fully open, the bloom ranges from about 6.5 to about 11.2 cm. in diameter. Petalage is very double with about 37 to 113 petals and about 5 to 48 petaloids irregularly arranged. When partially open, the bloom form is moderately globular to somewhat ovoid to cupped, and the petals are moderately tightly spiraled to cupped with petal edges somewhat reflexed outward. When fully open, the bloom form is more cupped, and the petals are loosely cupped to somewhat undulated to sometimes somewhat folded laterally with petal edges somewhat reflexed outward.

PETALS

The substance of the petals is moderately slight and of thin thickness, with upper surfaces moderately satiny and under surfaces moderately shiny. The petals are about 2.3 to about 4.8 cm. in length and about 1.3 to about 3.8 cm. in width at the widest point. Petal margins are entire.

The outer petals are moderately obovate in shape with rounded to sometimes lacerated apices and sometimes slightly notched with one notch.

The inner petals are moderately oblanceolate to somewhat obovate in shape with rounded to sometimes lacerated apices and sometimes slightly notched with one notch.

Petaloids are about 0.5 to about 3.6 cm. in length and about 0.4 to about 1.8 cm. in width at the widest point. Petaloids are irregularly shaped moderately oblanceolate to somewhat obovate to somewhat subulate with rounded to sometimes lacerated apices.

NEWLY OPENED FLOWER

The under surface color of the outer petals is between 60B and 66C at the base gradually suffusing toward the middle of the petal to between 74C and 64C. At the point where the petal attaches, there is a moderately small zone of between 3C and 4B. The color at the base of the upper surfaces of the outer petals is between 11A and 10A gradually suffusing to between 78D and 69B. At the point where the petal attaches, there is a somewhat small zone of between 11A and 10A.

The under surface color of the intermediate petals is between 60B and 66C. The color at the base of the upper surfaces of the intermediate petals is between 11A and 10A gradually suffusing to between 78D and 69B.

The under surface color of the inner petals is between 60B and 66C. The color at the base of the upper surfaces of the inner petals is between 11A and 10A gradually suffusing to between 64B and 66D.

The under and upper surface colors of the petaloids are similar in coloration to the upper and under surfaces of the inner petals.

The general tonality of the newly opened flower is between 64B and 66D.

THREE-DAY-OLD FLOWER

The under surface color of the outer petals is between 70C and 74D. At the point where the petal attaches, there is a moderately small zone of between 2D and 1D. The upper surface color of the outer petals is between 69B and 73B often lightly suffused with between 74D and 63A. At the point where the petal attaches, there is a moderately large zone of between 2D and 4D.

The under surface color of the intermediate and inner petals is between 70D and 68D. The upper surface color of the intermediate and inner petals is between 69B and 73B often lightly suffused with between 74D and 63A.

The under and upper surface colors of the petaloids are similar in coloration to the upper and under surfaces of the intermediate and inner petals.

The general tonality of the three-day-old flower is between 69B and 73B often lightly suffused with between 74D and 63A.

On the spent bloom, the petals usually drop off cleanly.

In December in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are few in number (average about 50) and are arranged regularly about the pistils; some are mixed with petaloids. The filaments are of somewhat short length (about 0.4 to about 0.7 cm.) most with anthers. Filaments are between 13B and 12A in color. The anthers are somewhat small for the class and all open approximately at the same time. Anther color when immature is near 22A on the external part and near 11D on the internal part. Anther color at maturity is near 165B on the external part and near 200A on the internal part. Pollen is moderate and between 18B and 19C in color.

FEMALE REPRODUCTIVE ORGANS

Pistils vary in number (average about 125). The styles are moderately even, long in length (about 0.6 to about 1.1 cm.), thin in caliper, and loosely bunched to somewhat separated. Stigma color is between 10A and 11A. Style color is between 154D and 1D often lightly suffused with near 60B. Ovaries are usually all enclosed in the calyx, although sometimes some may protrude from the calyx. The ovaries are small and between 158B and 158A in color.

Hips are of moderately short length (about 1.0 to about 1.6 cm.), rounded in form with a moderately flat top and base, and between 28A and 28B in color when ripe. The hip surface is smooth with thick fleshy walls.

The seeds are irregularly rounded, smooth in texture, approximately 6 to about 26 per hip, about 0.4 to about 0.7 cm. in diameter at the widest point and between 164B and 165C in color.

FOLIAGE

The compound leaves are usually comprised of three to seven leaflets and are borne abundantly. The seven-leaflet leaves are about 6.8 to about 15.0 cm. in length and about 4.8 to about 10.8 cm. in width at the widest point, moderately crisp to somewhat leathery in texture on both sides, and glossy in finish on the upper side and semi-glossy to somewhat matte in finish on the under side. The leaves have a pinnate venation pattern. The terminal leaflets are about 2.5 to about 6.3 cm. in length and about 1.6 to about 4.3 cm. in width at the widest point, shaped moderately ovate to somewhat oval with acute apices and rounded to somewhat acute bases. Their margins are usually simply serrate.

The upper surface color of the mature leaf is between 139A and 147A. The under surface color of the mature leaf is between 147B and 148D. The under and upper colors of the leaf veins on the mature leaf are similar in coloration to the upper and under surfaces colors of the mature leaf. The upper surface color of the young leaf is between 137B and 146A, often moderately suffused with between 187A and 187B. The under surface color of the young leaf is between 146C and 146B, often lightly suffused with between 187B and 183B. The under and upper colors of the leaf veins on the young leaf are similar in coloration to the upper and under surfaces colors of the young leaf.

The rachis is about 4.2 to about 8.8 cm. in length, about 0.1 to about 0.2 cm in width at the widest point, and rough. The upper side is deeply grooved with few hairs and stipitate glands on the edges of the grooves. The under side of the rachis is rough with few stipitate glands and small prickles. The rachis color is near 146D on the under side and near 137B on the upper side, often heavily suffused on the young leaves with between 187B and 187A.

The stipules are about 0.7 to about 2.1 cm. in length and of medium to somewhat wide width (about 0.5 to about 1.0 cm.) with moderately long straight points that usually turn out at an angle of more than 45 degrees and sometimes recurve toward the stem. The under and upper surface color of the stipule is between 137B and 137C. The upper and under surfaces of the stipules are smooth in texture.

The petiole is somewhat light to average in caliper and rough. The upper side is deeply grooved with few hairs and stipitate glands on the edges of the grooves. The under side of the petiole is rough with few stipitate glands and small prickles. The petiole is about 0.2 to about 1.5 cm. in length and about 0.1 to about 0.2 cm in width at the widest point. The petiole color is near 146D on the under side and near 137B on the upper side, often heavily suffused on the young leaves with between 187B and 187A.

The plant displays an average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has an upright slightly spreading medium to somewhat tall growing habit (about 120 to about 160 cm. in height and about 90 to about 120 cm. spread at the widest point), with full branching. It displays moderately vigorous growth and the canes are of medium size caliper for the class (about 1.5 to about 2.4 cm. in diameter at the widest point).

The color of the major stems is between 148A and 152A. The major stems are rough in texture and they bear some large prickles that are about 0.6 to about 1.0 cm. in length. The large prickles are angled slightly downward with a moderately long somewhat narrow oval base; prickle color is between 165B and 164A often moderately suffused with between 201B and 201C. The major stem bears very few small prickles of similar shape and coloration.

The color of the branches is between 137C and 146A. The branches are rough in texture and they bear some large prickles which are of similar shape to the large prickles on the major stems. The prickles are about 0.3 to about 0.6 cm. in length. Prickle color is between 152C and 152D sometimes lightly suffused with near 183C. The branches bear very few small prickles of similar shape and coloration.

The color of the new shoots is between 146D and 146C sometimes heavily suffused with between 187B and 187A. The new shoots are rough in texture and they bear few large prickles which are of similar size and shape to the large prickles on the branches; prickle color is between 152D and 153A sometimes lightly suffused with near 183C. The shoots bear very few small prickles of similar shape and coloration.

I claim:

1. A new and distinct Floribunda rose plant of the variety substantially as described and illustrated herein.

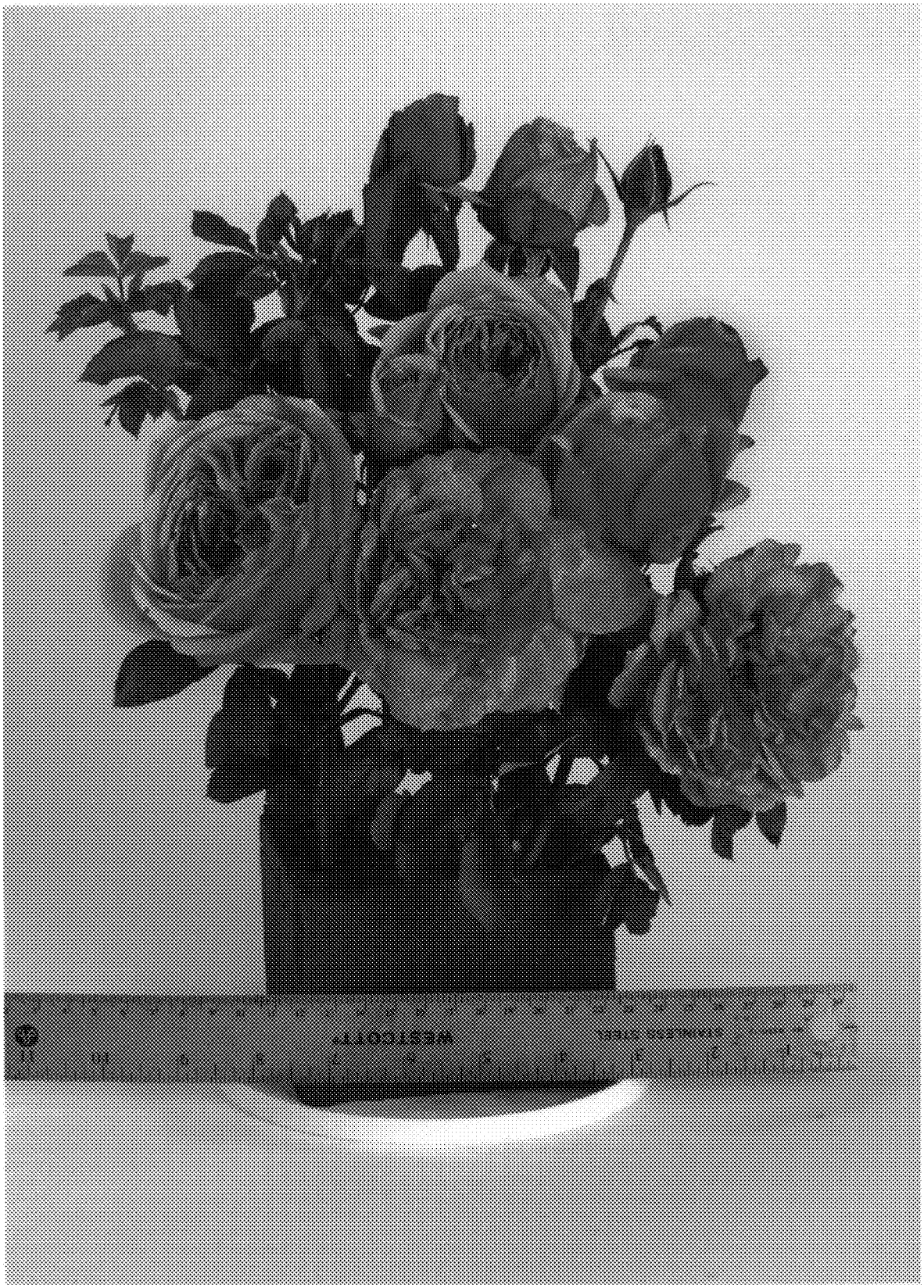

* * * * *